United States Patent [19]
Thireos et al.

[11] Patent Number: 6,004,795
[45] Date of Patent: Dec. 21, 1999

[54] DNA ENCODING CHITIN DEACETYLASE PREPARATIONS

[75] Inventors: George Thireos; Dimitri Kafetzopoulos, both of Heraklion, Greece

[73] Assignee: Institute for Molecular Biology and Biotechnology, Crete, Greece

[21] Appl. No.: 08/621,255

[22] Filed: Mar. 25, 1996

Related U.S. Application Data

[60] Division of application No. 07/989,991, Dec. 7, 1992, Pat. No. 5,525,502, which is a continuation-in-part of application No. 07/773,724, Oct. 9, 1991, Pat. No. 5,219,749.

[51] Int. Cl.⁶ ................................... C12N 9/78
[52] U.S. Cl. ................................................ 435/227
[58] Field of Search ................................ 435/227

[56] References Cited

U.S. PATENT DOCUMENTS

| | | | |
|---|---|---|---|
| 4,282,351 | 8/1981 | Muzzarelli | 536/20 |
| 4,368,322 | 1/1983 | Muzzarelli | 536/20 |
| 4,958,011 | 9/1990 | Bade | 536/20 |
| 5,219,749 | 6/1993 | Bouriotis et al. | 435/227 |
| 5,252,468 | 10/1993 | Fujishima et al. | 435/71.1 |
| 5,739,015 | 4/1998 | Srinivasan | 435/101 |

OTHER PUBLICATIONS

Araki et al., Eur. J. Biochem. 55:71–78, 1975.
Lombardi "Isolation and Characterization of a Chitin Deacetylase Activity from the Dimorphic Fungus, *Mucor Rouxii*," Master's Thesis, Dartmouth College, Jun. (1988).
Araki, Y., and Ito, E., "Chitin Deacetylase," *Methods in Enzymol.* 161: 510–514 (1988).
Kauss and Bauch "Chitin Deacetylase from Colletotrichum Lindemuthianum," *Methods of Enzymol.* 161: 518–523 (1988).
Pfaltz & Bauer Catalogue "Chitin Deacetylated," Edit. Div. Aceto. Chem. Waterbury, CT 06708 p. 81 NBR CO7640, 12th Edition (1991/1992).
Kafetzopoulos, D., et al., "The primary structure of a fungal chitin deacetylase reveals the function for two bactreial gene products,"*Proc. Natl. Acad. Sci. USA,* 90:8005–8008(1993).
Vazquez, M., et al., "Novel Organization of the Common Nodulation Genes in *Rhizobium leguminosarum* bv. phaseoli Strains," *Journal of Bacteriology,* 173(3):1250–1258(1991).
Scott, K. F., "Conserved nodulation genes from the non–legume symbiont *Bradyrhizobium sp.* (Parasponia)," *Nucleic Acids Research,* 14(7):2905–2919 (1986).
John, M., et al., "Rhizobium NodB protein involved in nodulation signal synthesis is a chitooligosaccharide deacetylase," *Proc. Natl. Acad. Sci. USA.,* 90: 625–629 (1993).
Plonski, B.A., et al., "Arsenic Sorption by Chitosan and Chitin Deacetylase Production by *Mucor ruoxii,*" *Biorecovery 1*: 239–253 (1990).
Kafetzopoulos, D., et al., "Isolation and Characterisation of Chitin Deacetylase from *Mucor rouxii,*" *J. Chem. Technol. Biotechnol.,* 56: 417–418 (1993).
Sambrook, J., et al., *"Molecular Cloning, A Laboratory Manual"*, Second Edition, Cold Spring Harbor Laboratory Press, Cold Spring Harbor, NY, pp. 11.1 to 11.19 (1989).
Schmidt, J., et al., "Rhizobium meliloti nodA and nodB genes are involved in generating compounds that stimulate mitosis of plant cells," *Proc. Natl. Acad. Sci. USA,* 85:8578–8582 (1988).
Lombardi, S.J., "Purification and Properties of the Chitin deacetylase of *Mucor Rouxii,*" Abstracts 89th Annual Meeting of the American Society for Microbiology, p. 251, Abstract No. K–37 (1989).
Roberts, G.A.F., *"Chitin Chemistry,"* Macmillan Press Ltd, London, pp. 6, 7, 281 (1992).

*Primary Examiner*—Robert A. Wax
*Attorney, Agent, or Firm*—Hamilton, Brook, Smith & Reynolds, P.C.

[57] ABSTRACT

Disclosed is the DNA sequence of an enzyme which catalyzes the conversion of chitin to chitosan. The enxyme exhibits substantial homology to the rhizobial nodB protein.

8 Claims, 4 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1203 base pairs
      (B) TYPE: nucleic acid
      (C) STRANDEDNESS: double
      (D) TOPOLOGY: linear    (ii) MOLECULE TYPE: cDNA    (ix) FEATURE:
      (A) NAME/KEY: CDS
      (B) LOCATION: 1..1200

(xi) SEQUENCE DESCRIPTION: SEQ ID NO:1:

```
GAC ACC TCC GCA AAT TAC TGG CAA TCA TTT ACT TCT CAA ATT AAT CCC      48
Asp Thr Ser Ala Asn Tyr Trp Gln Ser Phe Thr Ser Gln Ile Asn Pro
 1               5                  10                  15

AAG AAC ATC TCC ATT CCC TCT ATT GAG CAA ACT TCA TCC ATT GAC CCC      96
Lys Asn Ile Ser Ile Pro Ser Ile Glu Gln Thr Ser Ser Ile Asp Pro
             20                  25                  30

ACT CAA GAA TGT GCT TAC TAC ACT CCT GAT GCT TCA TTG TTC ACA TTC     144
Thr Gln Glu Cys Ala Tyr Tyr Thr Pro Asp Ala Ser Leu Phe Thr Phe
         35                  40                  45

AAC GCT TCC GAA TGG CCC TCT ATC TGG GAA GTC GCT ACT ACC AAT GGT     192
Asn Ala Ser Glu Trp Pro Ser Ile Trp Glu Val Ala Thr Thr Asn Gly
     50                  55                  60

ATG AAT GAG TCT GCC GAG TTC CTC AGT GTC TAC AAT TCT ATT GAC TGG     240
Met Asn Glu Ser Ala Glu Phe Leu Ser Val Tyr Asn Ser Ile Asp Trp
 65                  70                  75                  80

ACC AAG GCA CCC AAT ATT TCT GTG CGT ACC CTT GAC GCT AAC GGC AAC     288
Thr Lys Ala Pro Asn Ile Ser Val Arg Thr Leu Asp Ala Asn Gly Asn
                 85                  90                  95

TTG GAT ACC ACT GGT TAC AAT ACT GCT ACT GAC CCT GAT TGT TGG TGG     336
Leu Asp Thr Thr Gly Tyr Asn Thr Ala Thr Asp Pro Asp Cys Trp Trp
            100                 105                 110

ACA GCT ACC ACA TGT ACC TCT CCC AAG ATT TCT GAT ATC AAT GAC GAT     384
Thr Ala Thr Thr Cys Thr Ser Pro Lys Ile Ser Asp Ile Asn Asp Asp
        115                 120                 125

ATC TCC AAG TGT CCT GAA CCC GAG ACT TGG GGT TTG ACT TAC GAT GAT     432
Ile Ser Lys Cys Pro Glu Pro Glu Thr Trp Gly Leu Thr Tyr Asp Asp
    130                 135                 140

GGA CCT AAC TGC TCT CAC AAC GCT TTC TAT GAC TAC CTT CAA GAG CAA     480
Gly Pro Asn Cys Ser His Asn Ala Phe Tyr Asp Tyr Leu Gln Glu Gln
145                 150                 155                 160

AAG TTG AAG GCC TCC ATG TTT TAT ATT GGT TCC AAT GTT GTT GAC TGG     528
Lys Leu Lys Ala Ser Met Phe Tyr Ile Gly Ser Asn Val Val Asp Trp
                165                 170                 175

CCA TAC GGT GCT ATG CGT GGT GTT GTT GAT GGC CAT CAC ATT GCA TCC     576
Pro Tyr Gly Ala Met Arg Gly Val Val Asp Gly His His Ile Ala Ser
            180                 185                 190

CAC ACA TGG TCT CAC CCT CAA ATG ACA ACC AAG ACC AAT CAA GAG GTC     624
His Thr Trp Ser His Pro Gln Met Thr Thr Lys Thr Asn Gln Glu Val
        195                 200                 205

CTT GCT GAA TTC TAT TAT ACT CAA AAG GCC ATC AAG CTC GCT ACT GGT     672
Leu Ala Glu Phe Tyr Tyr Thr Gln Lys Ala Ile Lys Leu Ala Thr Gly
    210                 215                 220
```

```
TTG ACC CCT CGT TAC TGG CGT CCT CCT TAT GGT GAT ATC GAT GAT CGT      720
Leu Thr Pro Arg Tyr Trp Arg Pro Pro Tyr Gly Asp Ile Asp Asp Arg
225                 230                 235                 240

GTT CGT TGG ATT GCC TCT CAA TTA GGT TTA ACT GCT GTT ATT TGG AAC      768
Val Arg Trp Ile Ala Ser Gln Leu Gly Leu Thr Ala Val Ile Trp Asn
            245                 250                 255

CTC GAT ACT GAT GAT TGG TCT GCT GGT GTC ACT ACT ACT GTC GAA GCT      816
Leu Asp Thr Asp Asp Trp Ser Ala Gly Val Thr Thr Thr Val Glu Ala
        260                 265                 270

GTT GAG CAA AGT TAT TCC GAT TAT ATT GCT ATG GGT ACC AAT GGT ACT      864
Val Glu Gln Ser Tyr Ser Asp Tyr Ile Ala Met Gly Thr Asn Gly Thr
    275                 280                 285

TTT GCC AAC AGT GGT AAC ATT GTA TTG ACC CAT GAA ATC AAC ACA ACT      912
Phe Ala Asn Ser Gly Asn Ile Val Leu Thr His Glu Ile Asn Thr Thr
290                 295                 300

ATG AGT CTC GCT GTC GAG AAC TTG CCC AAG ATC ATT TCT GCC TAT AAA      960
Met Ser Leu Ala Val Glu Asn Leu Pro Lys Ile Ile Ser Ala Tyr Lys
305                 310                 315                 320

CAA GTC ATC GAT GTC GCT ACC TGT TAC AAC ATT TCT CAC CCT TAC TTT     1008
Gln Val Ile Asp Val Ala Thr Cys Tyr Asn Ile Ser His Pro Tyr Phe
            325                 330                 335

GAA GAC TAC GAA TGG ACC AAT GTC TTG AAC GGC ACA AAA TCT TCT GCT     1056
Glu Asp Tyr Glu Trp Thr Asn Val Leu Asn Gly Thr Lys Ser Ser Ala
        340                 345                 350

ACC GCC AGT GGA TCT GCT ACT TCT GCT AGT GCT TCT GGA GGC GCT ACT     1104
Thr Ala Ser Gly Ser Ala Thr Ser Ala Ser Ala Ser Gly Gly Ala Thr
    355                 360                 365

ACC GCT GCC GCT CAT ATC CAA GCT TCT ACT AGC GGC GCC ATG TCT GTC     1152
Thr Ala Ala Ala His Ile Gln Ala Ser Thr Ser Gly Ala Met Ser Val
370                 375                 380

CTT CCC AAC CTC GCC TTG ATC TCT GCC TTC ATT GCT ACC CTG TTG TTT     1200
Leu Pro Asn Leu Ala Leu Ile Ser Ala Phe Ile Ala Thr Leu Leu Phe
385                 390                 395                 400

TAG                                                                  1203
```

(2) INFORMATION FOR SEQ ID NO:2:

(i) SEQUENCE CHARACTERISTICS:
        (A) LENGTH: 400 amino acids
        (B) TYPE: amino acid
        (D) TOPOLOGY: linear     (ii) MOLECULE TYPE: protein     (xi) SEQUENCE DESCRIPTION: SEQ ID NO:2:

```
Asp Thr Ser Ala Asn Tyr Trp Gln Ser Phe Thr Ser Gln Ile Asn Pro
1               5                   10                  15

Lys Asn Ile Ser Ile Pro Ser Ile Glu Gln Thr Ser Ser Ile Asp Pro
            20                  25                  30

Thr Gln Glu Cys Ala Tyr Tyr Thr Pro Asp Ala Ser Leu Phe Thr Phe
        35                  40                  45

Asn Ala Ser Glu Trp Pro Ser Ile Trp Glu Val Ala Thr Thr Asn Gly
    50                  55                  60

Met Asn Glu Ser Ala Glu Phe Leu Ser Val Tyr Asn Ser Ile Asp Trp
65                  70                  75                  80

Thr Lys Ala Pro Asn Ile Ser Val Arg Thr Leu Asp Ala Asn Gly Asn
            85                  90                  95

Leu Asp Thr Thr Gly Tyr Asn Thr Ala Thr Asp Pro Asp Cys Trp Trp
            100                 105                 110

Thr Ala Thr Thr Cys Thr Ser Pro Lys Ile Ser Asp Ile Asn Asp Asp
```

-continued

```
                115                 120                 125
Ile Ser Lys Cys Pro Glu Pro Glu Thr Trp Gly Leu Thr Tyr Asp Asp
    130                 135                 140

Gly Pro Asn Cys Ser His Asn Ala Phe Tyr Asp Tyr Leu Gln Glu Gln
145                 150                 155                 160

Lys Leu Lys Ala Ser Met Phe Tyr Ile Gly Ser Asn Val Val Asp Trp
                165                 170                 175

Pro Tyr Gly Ala Met Arg Gly Val Val Asp Gly His His Ile Ala Ser
                180                 185                 190

His Thr Trp Ser His Pro Gln Met Thr Thr Lys Thr Asn Gln Glu Val
        195                 200                 205

Leu Ala Glu Phe Tyr Tyr Thr Gln Lys Ala Ile Lys Leu Ala Thr Gly
    210                 215                 220

Leu Thr Pro Arg Tyr Trp Arg Pro Pro Tyr Gly Asp Ile Asp Asp Arg
225                 230                 235                 240

Val Arg Trp Ile Ala Ser Gln Leu Gly Leu Thr Ala Val Ile Trp Asn
                245                 250                 255

Leu Asp Thr Asp Asp Trp Ser Ala Gly Val Thr Thr Thr Val Glu Ala
                260                 265                 270

Val Glu Gln Ser Tyr Ser Asp Tyr Ile Ala Met Gly Thr Asn Gly Thr
        275                 280                 285

Phe Ala Asn Ser Gly Asn Ile Val Leu Thr His Glu Ile Asn Thr Thr
    290                 295                 300

Met Ser Leu Ala Val Glu Asn Leu Pro Lys Ile Ile Ser Ala Tyr Lys
305                 310                 315                 320

Gln Val Ile Asp Val Ala Thr Cys Tyr Asn Ile Ser His Pro Tyr Phe
                325                 330                 335

Glu Asp Tyr Glu Trp Thr Asn Val Leu Asn Gly Thr Lys Ser Ser Ala
                340                 345                 350

Thr Ala Ser Gly Ser Ala Thr Ser Ala Ser Ala Ser Gly Gly Ala Thr
            355                 360                 365

Thr Ala Ala Ala His Ile Gln Ala Ser Thr Ser Gly Ala Met Ser Val
    370                 375                 380

Leu Pro Asn Leu Ala Leu Ile Ser Ala Phe Ile Ala Thr Leu Leu Phe
385                 390                 395                 400
```

DNA ENCODING CHITIN DEACETYLASE PREPARATIONS

This application is a division of application Ser. No. 07/989,991 filed Dec. 7, 1992 now U.S. Pat. No. 5,525,502, which is a Continuation-in-Part of Ser. No. 07/773,724 filed on Oct. 9, 1991, now U.S. Pat. No. 5,219,749.

BACKGROUND OF THE INVENTION

Next to cellulose, chitin is the world's most abundant, easily obtained, and renewable biological material. It is a natural product synthesized by a wide variety of organisms. Several billion tons of the material are produced annually. Chitin is a carbohydrate polymer, the N-acetylated polymer of β(1→4) linked N-acetylglucosamine, or poly-N-acetyl glucosamine. In plants, chitin is a cell wall constituent replacing cellulose or sometimes occurring together with cellulose. In animals, chitin is usually organized as a cuticle at one surface of the epithelial tissue. Although structurally similar to cellulose, chitin has distinctly different chemical properties. It is an extremely insoluble material, with limited industrial applicability.

The deacetylated derivative of chitin, chitosan, is a much more tractable material with a broad and impressive array of practical applications. Chitosan is positively charged, thus, it can be used as a protein precipitant and a metal chelating agent. It can be formulated as a solution, gel, membrane, film or fiber. Such formulations are useful, for example, in the areas of precious metal recovery, crop protection, chromatography and enzyme immobilization. Chitosan is a biologically benign, non-immunogenic, material making it ideal for use in the agricultural, food, drug and cosmetic industries. It can form complexes with other natural polymers, such as collagen and keratin, to form materials with unique biomedical properties. For example, such materials can be used as wound healing accelerants, components of artificial skin and blood vessels, anticoagulants, and controlled drug release vehicles.

At present the bulk of the chitosan produced worldwide is prepared from crustacean shell material. Chitin comprises about 20–50% of the dry weight of crustacean cuticles, the balance being primarily calcium carbonate, calcium phosphate and other proteins. Chitin is first isolated by treating ground crustacean shells with dilute acid and alkali to remove proteins and minerals. The raw chitin is then deacetylated by exposure to concentrated alkali at high temperature to generate chitosan. Although the chitosan produced in this manner has many useful features, it is impossible to effectively control the production process, which leads to the production of a material having a broad range of molecular weight and a heterogenous extent of deacetylation. Such a product is not of great value, since many of the potentially important applications, particularly in the biomedical area, require uniform material with very specific physical and chemical properties.

SUMMARY OF THE INVENTION

The subject invention relates to an isolated DNA sequence encoding an enzyme which catalyzes the conversion of chitin to chitosan. Specific embodiments include DNA sequences which are characterized by the ability to hybridize to the DNA sequence represented in SEQ ID NO: 1 under stringent hybridization conditions. The invention also relates to a DNA expression construct encoding an enzyme having the specificity described above, or biologically active portions thereof.

The invention also relates to a method for converting chitin to chitosan by contacting chitin with an enzyme having a chitin deacetylase activity. In this method, the enzyme is produced by recombinant DNA techniques in which an isolated DNA sequence encoding the enzyme, or a biologically active portion thereof, is expressed from a DNA expression construct.

Detailed Description of the Invention i) Purification of Chitin Deacetylase

The present invention was made possible by the discovery of a method for purifying chitin deacetylase from a cellular extract of an organism which produces chitin deacetylase. The enzyme chitin deacetylase is produced by a variety of genera including, for example, *Mucor, Phycomyces, Absidia,* and *Choanephora*. Other potentially useful genera include *Zygorhynchus, Actinomucor, Circinella, Rhizopus, Colletotrichum* and *Rhizomucor*.

A preferred source for chitin deacetylase is the cell wall of fungal mycelia. Such mycelia are produced in great quantities as a byproduct of the fermentation industry. The growth of *Mucor rouxii* in standard fermentors has been described in the literature. The use of a fungus such as *Mucor rouxii* offers a number of advantages. The organism can be grown using inexpensive nutrients. It can be grown to a high cell density (grams of cell dry weight per liter of culture medium) in a large scale fermentation system. The culture time required to achieve high cell density is as low as 12 hours/batch.

Initially, cellular extract is prepared from an organism which produces chitin deacetylase. For example, if the organism is a fungus (e.g., *Mucor rouxii*) mycelial cells are disrupted in the presence of an extraction buffer. The extraction buffer may contain protease inhibitors, other degradative enzyme inhibitors and stabilizers to maintain enzyme activity and facilitate its extraction. Non-soluble material is removed from the liquid phase of the extraction mixture, for example, by filtration or centrifugation.

The cellular extract is subjected to a thermal cycling step which results in the precipitation of undesirable protein (i.e., protein other than chitin deacetylase). For example, as described in the Examples below, the extract can be incubated at about 50° C. for a period of about 15–30 minutes. The precipitated protein is subsequently removed, for example, by filtration or centrifugation.

It is well known that the solubility properties of proteins in solutions having high salt concentrations vary over a wide range. This difference in solubility can be exploited to achieve separation of protein in a solution by precipitation at high ionic strength. Many salts can be used for this purpose, but ammonium sulfate is preferred by virtue of the fact that it does not appreciably alter pH, it is highly soluble, and it does not destabilize proteins.

Applicants' have determined that an ammonium sulfate concentration of about 2.1 M effectively precipitates a wide variety of proteins from the liquid phase described above, without precipitating the chitin deacetylase. Proteins which precipitate in an ammonium sulfate concentration of about 2.1 M are removed from the solution by standard techniques (e.g., filtration or centrifugation).

The liquid phase which is recovered following the ammonium sulfate precipitation is subjected to hydrophobic interaction chromatography. Hydrophobic interaction chromatography is widely employed for the purification of macromolecules on the basis of their varying strength of hydrophobic interaction with hydrophobic groups attached to an uncharged gel matrix. This technique is usually performed in the presence of moderately high concentrations of anti-chaotropic salts (salt promoted adsorption chromatography). Several factors influence the chromatographic behavior of proteins and peptides on hydrophobic adsorbents. These factors include ligand structure, ligand density, sample characteristics, flow rate, salting-out effect, ionic strength, temperature and pH. An example of a hydrophobic column resin is Phenyl Sepharose®6 Fast Flow. Material bound by a hydrophobic adsorbent is removed from the column by passing, for example, water over the column.

Following hydrophobic interaction chromatography, the solution containing the chitin deacetylase is further purified by ion-exchange chromatography. An ion exchanger is a solid support that has chemically bound charged groups to which ions are electrostatically bound. A negatively charged group will exchange positive ions and is a cation exchanger. A positively charged group will exchange negative ions and is an anion exchanger. Ion exchangers can be characterized as strong or weak ion exchangers. Strong ion exchangers function over a wide pH range and thus are useful for isolating a weakly ionized substance that requires very low or high pH for ionization.

The pH of the material which is recovered from the hydrophobic column is adjusted to about 8 and passed over a strong anion exchange column (e.g., Q Sepharose® Fast Flow). Fractions are collected and assayed for chitin deacetylase activity as described in the Exemplification section below. Fractions possessing chitin deacetylase activity are pooled and the pH of the pooled fractions is adjusted to about 3.5. The solution is then passed over a column which contains a strong cation exchange resin (e.g., S Sepharose® Fast Flow) and the flow through is collected. When analyzed by polyacrylamide gel electrophoresis, the flow through fraction contains an electrophoretically homogeneous protein species. The term essentially pure, as used herein, refers to a chitin deacetylase preparation which resolves substantially as a single band when analyzed by gel electrophoresis.

In a second method of purification, Applicants have employed purified immunoglobulin specifically reactive with chitin deacetylase. Immunoglobulin having the desired properties can be produced by immunizing an animal with essentially pure chitin deacetylase. Immunoglobulin having the desired properties can be attached to a solid support to form an immunoadsorbent. The immunoadsorbent can then be used to purify the enzyme from a crude extract by conventional methods.

Chitin deacetylase, prepared as described herein, can be used in a method for converting chitin to chitosan. Reaction parameters affecting enzyme activity are discussed in the Examples. Prior to the discovery which forms the basis of the subject invention, it was known in the art that a variety of organisms produce an enzyme having the ability to deacetylate chitin thereby converting chitin to chitosan. This enzyme, generally referred to as chitin deacetylase, is produced by a variety of genera including, for example, *Mucor, Phycomyces, Absidia,* and *Choanephora*. Other potentially useful genera include *Zygorhynchus, Actinomucor, Circinella, Rhizopus, Colletotrichum* and *Rhizomucor*.

A preferred source for chitin deacetylase is the cell wall of fungal mycelia. Such mycelia are produced in great quantities as a byproduct of the fermentation industry. The growth of *Mucor rouxii* in standard fermentors has been described in the literature.

ii) Chitin Deacetylase Production by Recombinant DNA Techniques

The production of an enzyme having chitin deacetylase activity by recombinant DNA techniques offers a variety of advantages over the purification of the enzyme from an organism in which it is naturally produced. For example, by using recombinant techniques, it is possible to produce the enzyme in a well characterized system such as *E. coli*. The use of this bacterial cell offers production advantages as compared with known chitin deacetylase producers such as *Mucor rouxii*.

In order to produce chitin deacetylase by recombinant DNA techniques, it is first necessary to isolate the gene which encodes the deacetylase. Example 4, presented below, describes experiments which were carried out in order to accomplish the isolation of this gene. The amino-terminal amino acid sequence was determined using conventional biochemical techniques to analyze an essentially pure preparation of the enzyme prepared as described above. The DNA sequence was determined and is presented in SEQ ID NO: 1. The DNA sequence disclosed in SEQ ID NO: 1 can be isolated by the methods described below, or by using the polymerase chain reaction amplification method. Primer sequences to be used in such an amplification reaction can be determined by reference to the DNA Sequences Listing below.

The scope of the invention encompasses an isolated DNA sequence encoding an enzyme having a chitin deacetylase activity, or a biologically active portion thereof, which is characterized by the ability to hybridize to the DNA sequence represented in SEQ ID NO: 1 under stringent hybridization conditions. DNA sequences which hybridize to the listed sequences under stringent hybridization conditions are either perfectly complementary, or highly homologous to the listed sequence. Homologous, as used herein, refers to DNA sequences which differ from the listed sequence, but the difference has no substantial effect on the biological activity (i.e., deacetylase activity) of the encoded protein. One possible set of stringent hybridization conditions is 50% formamide, 5 X SSPE (1 X SSPE is 0.15 M NaCl, 1 mM Na-EDTA, 10 mM Na-phosphate, pH 7.0), 5 X Denhardt's solution (0.1% polyvinylpyrrolidone, 0.1% Ficoll) at 45°.

The identification of biologically active fragments of the enzyme can be determined by conventional techniques. For example, deletions can be generated in the portion of the expression construct which encodes the enzyme. The deletion construct is then expressed and assayed for chitin deacetylase activity.

The isolated DNA sequences which fall within the scope of this invention can be used to express the encoded deacetylase in large quantities in either prokaryotic or eukaryotic host cells. For this purpose, the DNA is inserted into a prokaryotic or eukaryotic expression vector, with the appropriate regulatory signals, and used to transform cells. A variety of appropriate vectors and regulatory signals have been previously developed for this purpose and are well known to those skilled in the art.

Through the use of conventional techniques, the deacetylase of this invention can be overexpressed, for example, in E. coli to the extent that they represent a substantial proportion of the total cellular protein. The purification of a protein which is expressed at such substantial levels, and for which a simple assay system is established, is a straightforward matter to one skilled in the art.

In another aspect, the invention relates to methods for converting chitin to chitosan. In the claimed methods, chitosan is contacted with an enzyme having chitin deacetylase activity, the enzyme being produced by recombinant DNA techniques in which an isolated DNA sequence encoding the enzyme, or a biologically active portion thereof, is expressed from a DNA expression construct. The scope of this aspect of the invention includes not only the use of DNA characterized by the ability to hybridize to the DNA sequence represented in SEQ ID NO: 1 under stringent hybridization conditions, but also isolated DNA sequences which are characterized by the ability to hybridize to a DNA sequence encoding a rhizobial nodB protein. DNA sequence information relating to the NodABC locus has been published and submitted to database services. Examples of such publications include: Goethals et al., *Mol. Gen. Genet.* 219: 289–298 (1989); Krishnan et al. *Plant Microb. Interact.*; Surin et al., *Mol. Microbiol.* 2: 173–283 (1988); Rossen et al., *Nucl. Acids Res.* 12: 9497 (1984); Evans et al., *Gene* 43: 95–101 (1986); Shearman et al., *EMBO J.* 5: 647 (1986); Toeroek et al., *Nucl. Acids Res.* 12: 9509 (1984); Egelhoff et al., *DNA* 4: 241 (1985); Schofield et al., *Nucl. Acids Res.* 14: 2891 (1986); Scott, *Nucl. Acids Res.* 14: 2905 (1986); and Vasquez et al., *J. Bacteriol.* 173: 1250 (1991).

The invention is further illustrated by the following Examples.

EXAMPLES

Example 1: First Method for Purifying Chitin Deacetylase

Fermentation of *Mucor rouxii*

*Mucor rouxii* was obtained from the American Type Culture Collection (ATCC 24905). The fungus was grown in minimal medium as described by Bartnicki-Garcia and Nickerson (*Bacteriol.* 84: 841–858 (1962)) in 16 liters batches. Media was inoculated with $2 \times 10^8$ spores per liter and was stirred and aerated with sterile air for 24 hours at 28° C. Mycelia were harvested at mid-log phase by filtration. Cultures yielded approximately 20 grams of mycelia (wet weight) per liter.

Extraction and Purification of Chitin Deacetylase 400 grams of mycelia were extracted by blending with 600 grams of glass beads and 700 ml of extraction buffer containing 50 mM Tris HCl (pH 7.8), 100 mM NaCl and 0.2 mM PMSF for one hour over ice. After the extraction was completed the glass beads were settled and removed and the extract was centrifuged for 30 minutes at 8000 g at 4° C. The supernatant (750 ml) is referred to as the crude extract.

Figure 1:
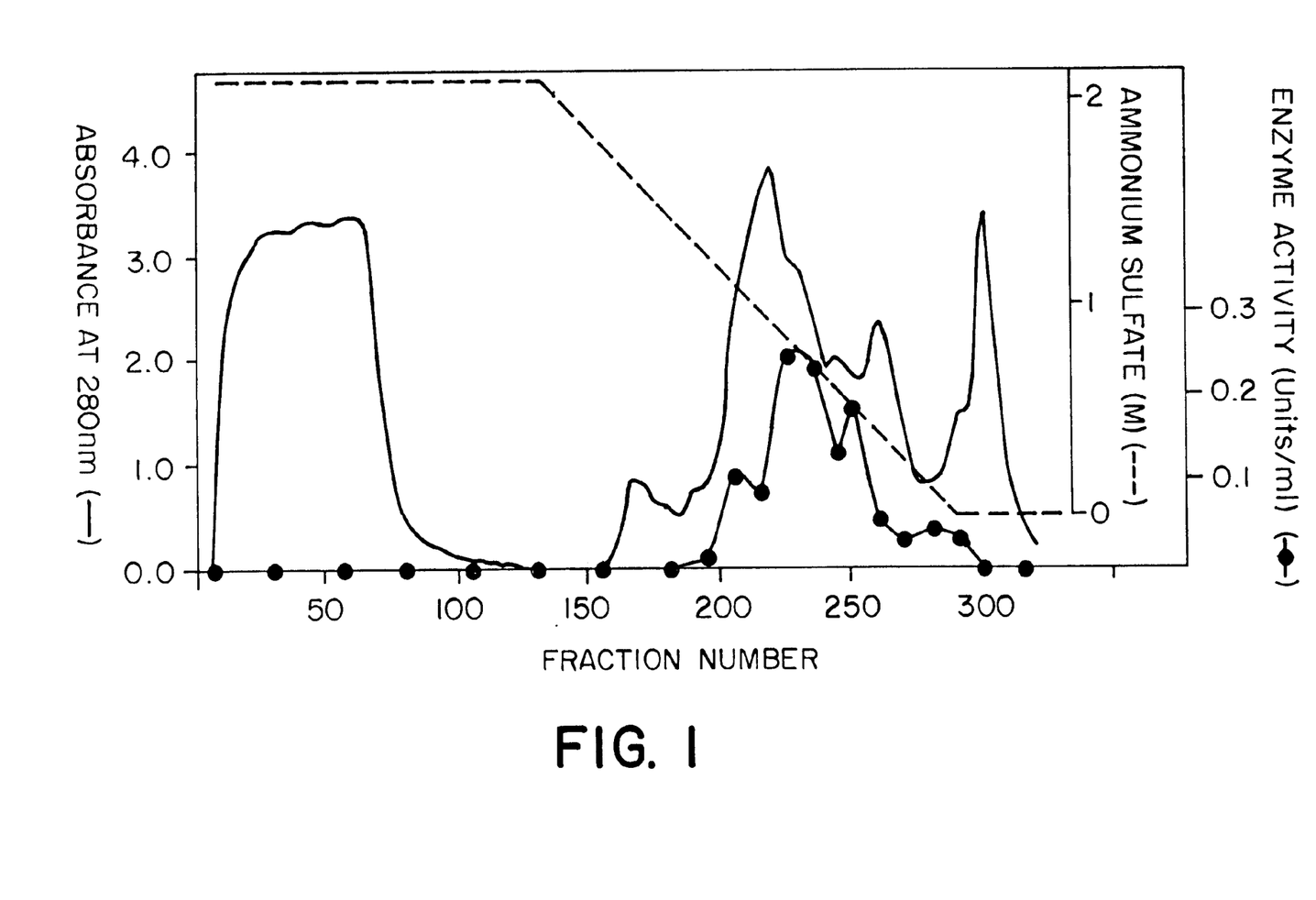
FIG. 1 is a diagram representing the elution profile from a Phenyl Sepharose® CL-4B column.

The crude extract was then incubated in a waterbath set at 50° C. for 30 minutes and the precipitated material was removed by centrifugation at 8000 g for 30 minutes at 4° C. The supernatant from the 50° C. incubation was made 2.1 M in ammonium sulfate and the precipitated proteins were removed by centrifugation at 10,000 g for 45 minutes. The supernatant (850 ml) was then passed over a column (44× 230 mm) of Phenyl Sepharose®CL-4B equilibrated with 20 mM Tris HCl (pH 7.5) containing 2.1 M ammonium sulfate. After the column was washed with the buffer mentioned above, the retained proteins were eluted with a 2100 ml linear gradient of decreasing ammonium sulfate concentration. Flow rate was 250 ml/h and fractions of 14 ml were collected. The elution profile is shown in FIG. 1. Chitin deacetylase activity was detected in fractions 195–295 which were pooled for further purification. The protein content was followed by a UV monitor at 280 nm.

Chitin deacetylase activity was estimated using as substrate partially O-hydroxyethylated chitin (glycol chitin) radiolabeled in N-acetyl groups. The substrate preparation as well as the assay conditions were as described by Araki and Ito (*Eur. J. Biochem.* 55:71–78 (1975)) with the following modifications. The assay mixture contained 0.1 mg/ml BSA buffered by 25 mM sodium glutamate at pH 4.5 (50° C.). Incubation time was 30 minutes at 50° C.

Figure 2:
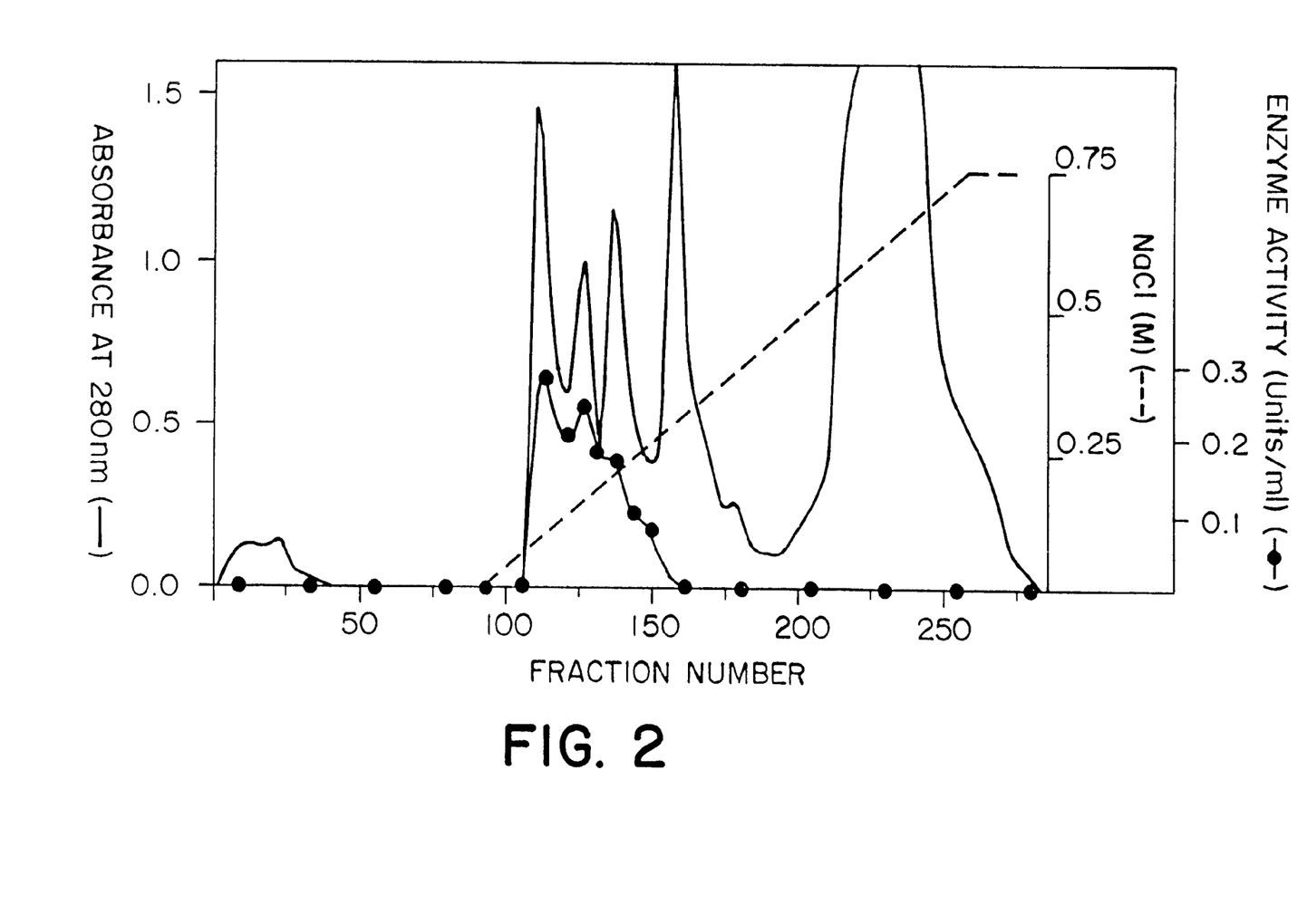
FIG. 2 is a diagram representing the elution profile from a Q Sepharose® Fast Flow column.

The sample of partially purified chitin deacetylase from the previous step was dialyzed against 20 mM Tris HCl (pH 8), and then passed over a column of Q Sepharose® Fast Flow (26×340 mm) equilibrated with the same buffer. After the column was washed, a linear gradient of NaCl (2000 ml, 0–0.75 M) buffered with 20 mM Tris HCl (pH 8), was established. Flow rate was 300 ml/h and fractions of 11.5 ml were collected. The elution profile is shown in FIG. 2. Chitin deacetylase activity was detected in fractions 105–150 corresponding to ~0.13 M NaCl. These fractions were pooled for further processing.

Figure 3:
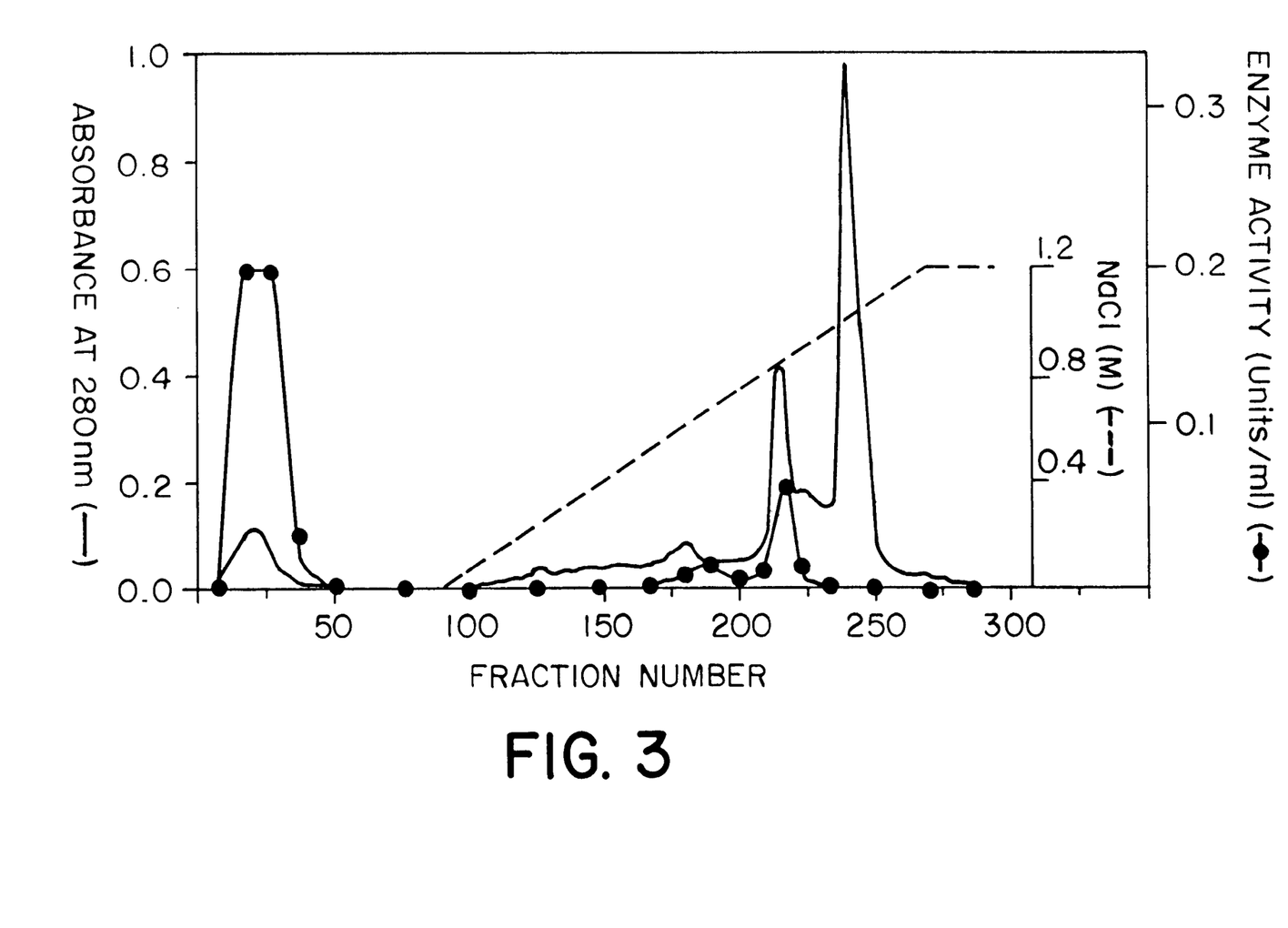
FIG. 3 is a diagram representing the elution profile from an S Sepharose® Fast Flow column.
Figure 4:
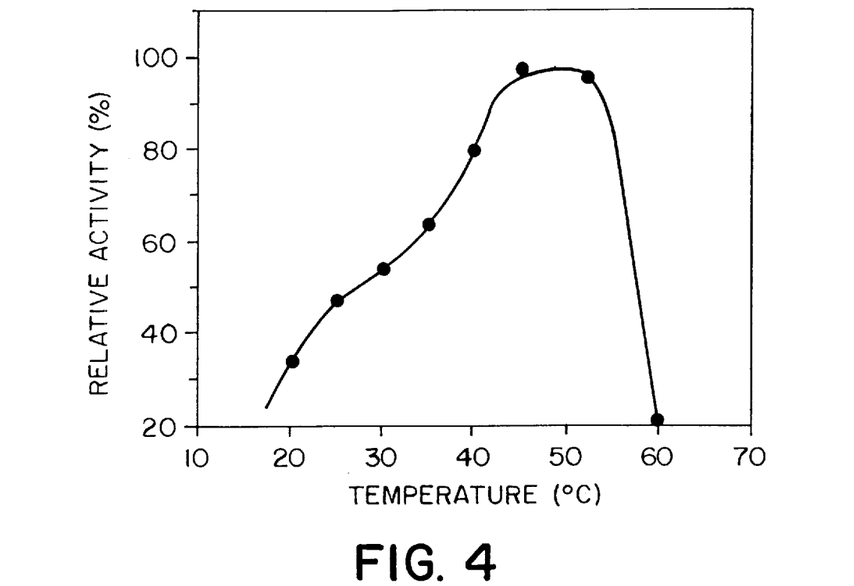
FIG. 4 is a diagram which represents the temperature dependence of chitin deacetylase activity.
Figure 5:
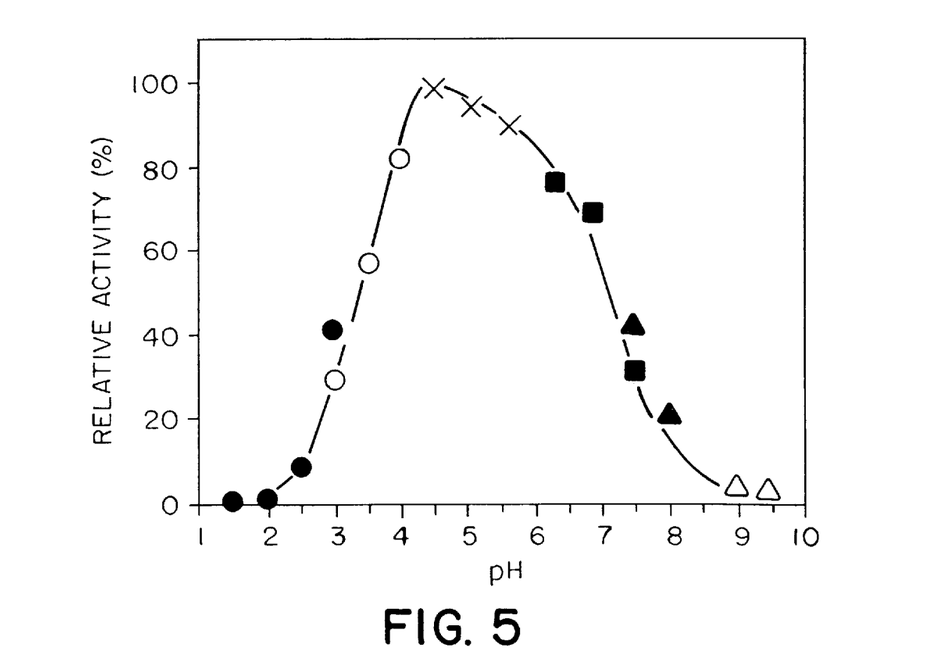
FIG. 5 is a diagram which represents the pH dependence of chitin deacetylase activity.

The pooled fractions were dialyzed against 25 mM sodium formate buffer, (pH 3.5), and the sample was loaded on an S Sepharose® Fast Flow column (26×280 mm) equilibrated with the same buffer. The column was eluted at a flow rate of 250 ml/h with a linear gradient of NaCl (2000 ml, 0–1.2 M) in the buffer mentioned above. Fractions of 12 ml were collected. The elution profile is shown in FIG. 3. The majority of chitin deacetylase activity was not retained by the column and was detected in the flow through fractions in an electrophoretically homogenous form.

Characterization of Purified Enzyme a) molecular weight

The results of the purification scheme are summarized in Table 1. The enzyme purified by this procedure was judged to be electrophoretically homogeneous, as tested by both native and SDS-PAGE. On a gradient (5–20%) SDS polyacrylamide gel the enzyme band migrated at a distance corresponding to molecular weight of ~75 kDa. When purified chitin deacetylase was subjected to gel filtration on Sephacryl® S-200 HR it was eluted as a single peak with an apparent size of ~80 kDa indicating that the native enzyme exists as a monomer.

TABLE 1

Purification of chitin deacetylase

| Step | Total protein (mg) | Total enzyme activity (units[a]) | Specific activity units/mg | Yield (%) | Purification (-fold) |
|---|---|---|---|---|---|
| Crude extract | 10380 | 345 | 0.033 | 100 | 1 |
| 50° C. treatment | 4719 | 240 | 0.051 | 69.6 | 1.54 |
| Phenyl Sepharose ® | 1374 | 150 | 0.11 | 43.5 | 3.3 |
| Q Sepharose ® | 279 | 80 | 0.29 | 23.2 | 8.8 |
| S Sepharose ® | 12.6 | 40.7 | 3.23 | 11.8 | 97.9 |

[a]One unit of the enzyme activity was defined as the amount of the enzyme required to produce 1 μmole of acetic acid per minute when incubated with 48 μg of glycol chitin under optimum pH (4.5) and temperature (50° C.) conditions.

b) carbohydrate content

Several pieces of evidence suggest that chitin deacetylase is a glycoprotein. After electrophoresis, the enzyme band gave a positive stain with periodate-Schiff's reagent on polyacrylamide gels. The enzyme was retained by a column of concanavalin A-Sepharoses® 4B and recovered as a single peak by elution with a gradient of α-methyl mannoside at a position corresponding to approximately 25 mM. As shown in Table 2, direct carbohydrate analysis of the enzyme revealed that the protein contains 6 residues of fucose, 85 residues of mannose and 22 residues of N-acetylglucosamine per molecule contributing approximately 30% to its molecular weight. Sialic acid and other sugars were not found in significant amounts.

Monosaccharide analysis was carried out by gas-liquid chromatography and gas-liquid chromatography-mass spectrometry. The sample was hydrolyzed in 4 M tri-fluoroacetic acid at 100° C. for 4 hours. The molar ratio of carbohydrates per molecule was estimated by direct carbo-hydrate and amino acid composition analysis.

TABLE 2

| Carbohydrate | mol/mol of protein | Nearest integer |
|---|---|---|
| Fucose | 5.81 | 6 |
| Mannose | 81.92 | 82 |
| N-Acetylglucosamine | 20.73 | 21 |
| Sialic acid | 0 | | c) immunoprecipitation of in vitro translation product

In order to determine the size of the chitin deacetylase polypeptide chain in an alternative manner, mRNA encoding the enzyme was translated in vitro followed by immunoprecipitation. mRNA was extracted from mycelia (15 g wet weight) harvested at the early log phase by grinding in liquid nitrogen. mRNA was purified by the guanidinium thiocyanate method of Chirwin et al. (*Biochem.* 18:5294–5299 (1979)) followed by pelleting in cesium chloride by ultracentrifugation. Poly (A)+ RNA (~120 μg) was isolated by 3 passes through an oligo(dT)-cellulose column as described by Aviv and Leder (*Proc. Natl. Acad. Sci., USA* 69:1408–1412 (1972)). In vitro translation of total mRNA was performed using nuclease treated rabbit reticulocyte lysate according to the manufacturer's instructions. In vitro translation products were labeled with $^{35}$S-methionine.

Polyclonal antisera was prepared by emulsifying pure chitin deacetylase (500 μg, 1 mg/ml in PBS) with an equal volume of Freund's complete adjuvant. The mixture was injected intradermally into a rabbit after preimmune serum was obtained. The animal was reimmunized and bled after four and six weeks with 200 μg of enzyme in Freund's incomplete adjuvant, also injected intradermally. Antisera obtained were monitored for the presence of anti-chitin deacetylase antibodies by ELISA and by enzyme activity inhibition assays.

After the in vitro translation reaction was completed, 10 μl of preimmune serum were added and the reaction was incubated for 30 minutes at room temperature. Antigen-antibody complexes were removed by centrifugation after adsorption to 10 μl of Protein A-Sepharose® added to the reaction. Specific polyclonal antiserum (10 μl) was then added to the supernatant which was subsequently incubated as described above. The new antigen-antibody complexes were collected using protein A-Sepharose® by centrifugation and then washed three times with 20 volumes of 25 mM Tris HCl (pH 7.5), 150 mM NaCl by resuspension and pelleting. Immunoprecipitates were boiled for 5 min in SDS-PAGE loading buffer and analyzed by gel electrophoresis. The gel was fixed for 30 min in 10% acetic acid, 30% methanol, incubated for 30 min in EN$^3$HANCE® (New England Nuclear) and then dried and exposed.

In vitro translation products were analyzed on a 12% SDS polyacrylamide gel followed by autoradiography. The material immunoprecipitated by the specific antiserum showed one band corresponding to molecular weight of ~49000 kDa that represents the size of the polypeptide chain prior to any post-translational modification.

d) enzyme activity characterization

The temperature optimum of the enzyme activity was estimated to be ~50° C. using labeled glycol chitin, as substrate as described above. The temperature dependence of the chitin deacetylase activity is shown graphically in FIG. 1. The pH optimum was estimated to be ~4.5, tested with a combination of overlapping buffers, as shown graphically in FIG. 2. Chitin deacetylase (5 mU) when incubated with 1 mg of partially chemically deacetylated chitosan (81%) for one hour, released 0.22 μmoles of acetic acid corresponding to an increment of ~5.3% in deacetylation degree. The enzyme was also active on microcrystalline chitin (colloidal chitin) and carboxymethyl chitin (soluble derivative).

e) amino acid composition

The amino acid composition of chitin deacetylase is shown in Table 3. Basic amino acids accounted only for ~8% of the total amino acids, a value ~40% lower than the average.

Amino acid composition of purified chitin deacetylase was determined after 24 hour hydrolysis with 6 M HCl at 100° C. The values are means of two different sample determinations. The number of residues per molecule of protein is based on the estimated molecular weight of 49000 Da from SDS-PAGE of the immunoprecipitated product from in vitro translation of mRNA.

TABLE 3

| Amino acid | Residues/molecule | Nearest integer |
|---|---|---|
| Aspartic acid | 56.01 | 56 |
| Threonine | 55.65 | 56 |
| Serine | 59.23 | 59 |
| Glutamic acid | 37.33 | 37 |
| Proline | 29.08 | 29 |
| Glycine | 31.62 | 32 |

TABLE 3-continued

| Amino acid | Residues/molecule | Nearest integer |
| --- | --- | --- |
| Alanine | 56.73 | 57 |
| Valine | 27.58 | 28 |
| Methionine | 5.09 | 5 |
| Isoleucine | 20.40 | 20 |
| Leucine | 20.89 | 21 |
| Tyrosine | 16.24 | 16 |
| Phenylalanine | 8.78 | 9 |
| Histidine | 7.31 | 7 |
| Lysine | 15.85 | 16 |
| Arginine | 5.87 | 6 |
| Half-Cysteine | 9.62 | 10 |
| Tryptophan | 7.77 | 8 |
| Total | | 472 |

Example 2 Production and Purification of Antibodies Reactive with Chitin Deacetylase An adult male white New Zealand rabbit was immunized with 500 µg (1 mg/ml in PBS) of purified chitin deacetylase, prepared as described in Example 1, from the fungus *Mucor rouxii*. The enzyme was emulsified with an equal volume of Freund's complete adjuvant in a total volume of 1 ml, and was administered to the animal intradermally. A further three booster doses of 150 µg of chitin deacetylase emulsified in Freund's incomplete adjuvant were administered at 4-week intervals. Test bleeds from the marginal ear vein were used to monitor serum antibody titer by ELISA. Control serum was taken prior to immunization.

The specificity of the antiserum produced was analyzed in a chitin deacetylase inhibition assay. Chitin deacetylase activity was assayed by measuring the radioactivity of [$^3$H]-acetic acid liberated from a water-soluble chitin derivative, glycol [acetyl-$^3$H] chitin. The reaction mixture contained 48 µg of glycol [acetyl-$^3$H] chitin, 1 nM magnesium chloride, 0.1 mg/ml BSA and was buffered by 25 mM sodium glutamate (pH 4.5) in a total volume of 50 µl. After incubation at 50° C. for 15 min, the reaction was terminated by the addition of 16 µl of HCl, 4 µl of acetic acid and 80 µl of water. Ethyl acetate (0.5 ml) was added to the mixture, and the solution was vigorously mixed with a vortex mixer for 5 minutes and centrifuged at 14,000 rpm. 4.5 ml of toluene-based liquid scintillation cocktail was added to 200 µl of the organic phase solution and swirled. The solution was transferred to a vial and measured for radioactivity in a liquid scintillation counter. One unit of enzyme releases 1.0 µmol of the acetic acid from glycol chitin per minute under the conditions described above. Specific activity was defined as the units of enzyme per milligram of protein. Protein was assayed by the so-called Lowry method using bovine serum albumin as a standard.

Antibody titer was monitored using a non-competitive ELISA. Chitin deacetylase was immobilized onto microtiter plates (Maxi Sorp, Nunc, Denmark) at 2 µg/ml of "coating" buffer (pH 9.6), containing 0.05 M sodium carbonate and sodium bicarbonate by incubation overnight at 4° C. Wells were washed out with 0.05% aqueous solution of Tween 80 followed by two washes with distilled water. After that 200 µl of blocking agent per well was incubated for 1 hour at room temperature. The blocking agent was 1 g of bovine serum albumin dissolved in 100 ml of 0.010 M PBS (pH 7.4). Wells were washed out as before. An anti-rabbit IgG conjugated to horseradish peroxidase was used to indirectly detect specific IgG bound to immobilized chitin deacetylase. The conjugate was diluted 10,000-fold in 0.010 M PBS (pH 7.4) and incubated at 100 µl per well for one hour at room temperature. Wells were washed out with H$_2$O/Tween 80 solution as before, followed by two washes with distilled water. Wells were aspirated and incubated with 100 µl of substrate/chromogen solution made up just prior to use. The reaction was stopped after 15 minutes by addition of 50 µl of 4 M sulfuric acid per well. Absorbance was read at 450 nm using an ELISA reader. The enzyme activity of a defined amount of purified chitin deacetylase was measured after incubation with various amounts of antiserum. These experiments confirmed that a component of the antiserum was specifically reactive with chitin deacetylase.

IgG was affinity-purified from rabbit serum using chitin deacetylase immobilized to cyanogen bromide-activated Sepharose 4B (Pharmacia Ltd.) according to manufacturer's instructions. A solution containing ten milligrams of purified chitin deacetylase was dialyzed against 2 lt of "coupling buffer" (pH 8.3), containing 0.1 M sodium bicarbonate and 0.5 M sodium chloride. Preswollen cyanogen bromide-activated Sepharose 4B equilibrated with coupling buffer was mixed with chitin deacetylase (1.4 mg protein/ml of gel) overnight at 4° C. by end over end rotation. This mixture was transferred to a scintered glass funnel and sucked dry under vacuum. The fluid was recovered and assayed for protein to assess coupling efficiency. The gel was washed thoroughly with coupling buffer and mixed as before for 2 hours with Tris-HCl buffer (0.1 M, pH 8.0) at room temperature. The gel was sucked dry and washed with coupling buffer. Protein noncovalently adsorbed to the gel was removed by washing the gel with alternating buffers of low (0.1 M sodium acetate, 0.5 M sodium chloride, pH 4.0) and high pH (0.1 M Tris, 0.5 M sodium chloride, pH 8.3). The chitin deacetylase-linked Sepharose 4B was transferred to a mini-column and washed with 0.025 M Tris-HCl (pH 7.4) which contained 0.02% sodium azide during storage at 4° C. The concentration of antibody in solution can be estimated by measuring $A_{280}$ using an average extinction coefficient for antibodies of 1.4 for 1 mg ml$^{-1}$ protein using a 1 cm path length cell.

Rabbit antiserum against chitin deacetylase obtained from various bleedings was separately precipitated by 40% saturation of ammonium sulfate. The immunoglobulin containing precipitate was dissolved and dialyzed extensively against 0.025 M Tris (pH 7.4), 0.2 M sodium chloride and subsequently passed through the chitin deacetylase-linked Sepharose 4B column (including protease inhibitors). The gel was washed with ten column volumes of 0.025 M Tris, 0.1 M sodium chloride (pH 7.4), until collected fractions gave negligible readings at 280 nm. Non-specifically bound proteins were eluted with 0.025 M Tris, 1 M sodium chloride, pH 7.4. A batch of IgG was eluted with two column volumes of 0.1 M glycine-hydrochloric acid buffer (pH 2.8). A further batch of higher affinity IgG was eluted with two column volumes of 0.2 M glycine-hydrochloric acid, pH 2.2. The term affinity, as used herein, refers to the functional affinity (avidity) as polyclonal antibodies were used. All fractions were immediately adjusted to pH 7.0 with 1 M Tris-HCl (pH 9.0). The two populations of IgG fractions were pooled separately and concentrated by ultrafiltration prior to dialysis against 0.025 M Tris (pH 7.4). The purified specific IgG shows the characteristic rabbit IgG pattern in SDS-PAGE. Pure specific IgG is stored at −20° C. at a concentration >1 mg/ml in 0.010 M Tris, 0.1 M sodium chloride (pH 7.4).

The coupling of chitin deacetylase to cyanogen bromide-activated Sepharose 4B was 90% efficient, producing chitin deacetylase-linked Sepharose 4B at 1.4 mg of chitin deacetylase/ml of gel. By the method presented here, about 2.0–6.5 mg of pure specific IgG were isolated from every 10 ml of antiserum with the elution of pH 2.8 (2.0% to 5.0% of total protein after ammonium sulfate precipitation). Total isolated specific IgG represents 4.5% to 8.0% of total protein after ammonium sulfate precipitation. The binding capacity of the chitin deacetylase-linked Sepharose 4B for anti-chitin deacetylase antibody was determined at 1.4 mg IgG/ml of gel.

Example 3 Second Method for Purifying Chitin Deacetylase

Frozen mycelia (2 gram), prepared as described in Example 1, was thawed, minced and homogenized in 10 ml of 0.05 M Tris-HCl buffer (pH 7.4) containing 0.5 mM PMSF, 0.1 mM NEM and 150 mM NaCl, using an improvised glass-bead miller (2 gram glass beads per gram of wet mycelia). All steps were performed at 4° C. This produced a homogenate which was centrifuged at 10,000 rpm for 30 minutes at 4° C. The supernatant (12.2 ml; 4.6 mg/ml; 56.0 mg) is referred to as the crude extract. The extract was then incubated in a waterbath set at 50° C. for 15 minutes and rapidly cooled on ice. Precipitated protein was removed by centrifugation at 35,000 rpm for 45 minutes at 4° C.

Five milligrams of the pure lower affinity rabbit IgG, described in Example 2, was dialyzed against the coupling buffer (pH 8.3) and mixed with 5 ml of swollen CNBr-activated Sepharose 4B to prepare an immunoadsorbent. The IgG was coupled by the method described for chitin deacetylase coupling. The coupling of IgG to activated Sepharose 4B was 85% efficient, producing IgG-linked Sepharose at 1 mg IgG/ml of gel. This immunoadsorbent was used for chitin deacetylase purification.

The supernatant described above (11.5 ml; 0.54 mg/ml; 6.2 mg) was loaded onto the immunoadsorbent (packed in a column of dimensions 2×1.6 cm; 5 ml) previously equilibrated in 25 mM Tris-HCl buffer (pH 7.4) containing 150 mM NaCl (buffer A). The column was washed with buffer A until no absorption of 280 nm was evident in the effluents (non-specifically bound proteins were eluted with 25 mM Tris-HCl pH 7.4, 1M NaCl). Specifically bound chitin deacetylase was eluted using 0.2 M glycine-HCl buffer (pH 2.8) at a flow rate of 35 ml/h. Eluate was immediately adjusted to pH 7.0 with 1 M Tris-HCl pH 9.0, dialyzed against buffer A and concentrated by ultrafiltration (300 μl; 40 μg/ml; 12 μg; 180 mU).

Purification of chitin deacetylase by immunoadsorption (table 4) produced a specific activity of 1500 m units/mg for the desorbed enzyme and a yield of about 30%. Assessment of chitin deacetylase purity by SDS-PAGE shows a single band. Purification of chitin deacetylase by conventional methods (table 1) produced a pure enzyme with a specific activity of 3.23 units/mg and a yield of 11.8%. The maximum binding capacity of the immunoadsorbent was determined at 42 μg of chitin deacetylase/ml of gel (4% of the antigen binding sites remain available for binding antigen after covalent immobilization to the matrix).

TABLE 4

Purification of Chitin Deacetylase By Immunoadsorption

| Step | Total Protein (mg) | Enzyme activity (munits) | Specific activity (munits/mg) | Yield (%) | Purification (fold) |
|---|---|---|---|---|---|
| Crude extract | 56.0 | 608 | 10.86 | 100.0 | 1.0 |
| 50° C. treatment | 6.2 | 540 | 87.10 | 88.8 | 8.1 |
| Immunoadsorbent | 0.012 | 180 | 1500.00 | 29.6 | 1400.0 |

Example 4

A purified preparation of chitin deacetylase was subjected to amino-terminal amino acid sequence analysis by conventional techniques. Based on the amino acid sequence information, degenerate oligonucleotides were synthesized and a cDNA clone corresponding to the chitin deacetylase mRNA was isolated from a *Mucor rouxii* cDNA library. The cDNA sequence was determined and this sequence is shown in SEQ ID NO: 1.

A search of the EMBL databank using the deduced amino acid sequence of chitin deacetylase revealed significant sequence similarities with nodB proteins of various rhizobial species. Multiple sequence alignments using all known nodB protein sequences and the chitin deacetlyase sequence highlighted the most significant similarities.

The nodb protein sequence (≈215 amino acids long) are well conserved between all rhizobial species examined, with identities ranging from 37–67% and overall similarities from 55–78%. Chitin deacetylase is a much longer polypeptide (400 amino acids) and the region which displays homology to the nodB gene products (up to 31% identity, 50% similarity) is located in the central part of the molecule. The amino-terminal (1–121 amino acid) and the carboxyl-terminal (≈50%) are conserved in chitin deacetylase. In contrast, six of nine predicted N-glycosylation sites are found in the non-conserved domains of chitin deacetylase suggesting that these glycosylated domains may be important for the specialized function of the enzyme in cell wall biosynthesis.

Equivalents

Those skilled in the art will know, or be able to ascertain, using no more than routine experimentation, many equivalents to the specific embodiments of the invention described herein. These and all other equivalents are intended to be encompassed by the following claims.

We claim:

1. An essentially pure chitin deacetylase preparation wherein the chitin deacetylase has a molecular weight of about 75–80 kilodaltons and is from *Murcor rouxii*.

2. An essentially pure chitin deacetylase preparation of claim 1 wherein the chitin deacetylase has a pI of about 3.0.

3. An essentially pure enzyme having the amino acid sequence of SEQ ID NO: 2.

4. An essentially pure enzyme comprising amino acids 121 through 325 of SEQ ID NO: 2 and having a chitin deacetylase activity present in *Mucor rouxii*.

5. A recombinant enzyme having the amino acid sequence of SEQ ID NO: 2.

6. A recombinant enzyme comprising amino acids 121 through 325 of SEQ ID NO: 2 and having a chitin deacetylase activity present in *Mucor rouxii*.

7. A recombinant enzyme having chitin deacetylase activity encoded by the DNA sequence represented in SEQ ID NO: 1.

8. An essentially pure preparation of chitin deacetylase, wherein the chitin deacetylase has a molecular weight of about 75–80 kilodaltons and is from *Mucor rouxii*, prepared by:

a) providing a *Mucor rouxii* mycelial extract;

b) adding ammonium sulfate to the extract to a concentration of about 2.1 M;

c) removing non-soluble material from the liquid phase;

d) passing the liquid phase from step c) over a hydrophobic column;

e) eluting the bound material from the hydrophobic column;

f) adjusting the pH of the eluted material from step e) to produce a solution having a pH of about 8;

g) passing the soltion from step f) over a strong anion exchange column;

h) collecting fractions from the strong anion exchange column and pooling fractions with chitin deacetylase activity;

i) adjusting the pH of the pooled fractions from step h) to about 3.5; and j) passing the solution from step i) over a strong carton exchange column and collecting the flow through.

* * * * *

UNITED STATES PATENT AND TRADEMARK OFFICE
CERTIFICATE OF CORRECTION

PATENT NO. : 6,004,795
DATED : December 21, 1999
INVENTOR(S) : George Thireos and Dimitri Kafetzopoulos It is certified that error appears in the above-identified patent and that said Letters Patent is hereby corrected as shown below:

In Claim 1, line 50 "Murcor" should be -- Mucor --.

In Claim 8, line 65 "carton" should be --- cation ---.

Signed and Sealed this

Thirtieth Day of January, 2001

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 6,004,795
DATED : December 21, 1999
INVENTOR(S) : George Thireos and Dimitri Kafetzopoulos It is certified that error appears in the above-identified patent and that said Letters Patent is hereby corrected as shown below:

Cover Page [54] and col. 1,   Delete "DNA Encoding Chitin Deacetylase Preparations" and insert --Chitin Deacetylase Preparations--.

Signed and Sealed this

Tenth Day of April, 2001

Attest:

NICHOLAS P. GODICI

*Attesting Officer*   *Acting Director of the United States Patent and Trademark Office*